United States Patent
Robidoux et al.

(12) 
(10) Patent No.: US 6,632,942 B2
(45) Date of Patent: Oct. 14, 2003

(54) ASYMMETRIC SYNTHESIS OF PIPERAZIC ACID AND DERIVATIVES THEREOF

(75) Inventors: Andrea L. C. Robidoux, Andover, MA (US); Siro Serafini, Vincenza IT (IT); Petra Dieterich, Abingdon (GB); Stefania Leonardi, Wallingford (GB); John Stibbard, Didcot (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/168,463

(22) Filed: Jun. 14, 2002

(65) Prior Publication Data

US 2003/0176691 A1 Sep. 18, 2003

Related U.S. Application Data

(63) Continuation of application No. PCT/US01/13330, filed on Apr. 25, 2001.
(60) Provisional application No. 60/202,104, filed on May 4, 2000.

(51) Int. Cl.$^7$ ..................... C07D 237/04; C07D 487/04
(52) U.S. Cl. ...................................... 540/500; 544/224
(58) Field of Search ........................... 544/224; 540/500

(56) References Cited

U.S. PATENT DOCUMENTS 4,692,438 A  9/1987  Hassall et al. ............... 514/183

FOREIGN PATENT DOCUMENTS

EP   0 570 764 A2   11/1993

OTHER PUBLICATIONS

Adams, C.E., et al., "Preparation of 1–(Benzyloxycarbonyl) Hexahydro–3–Pyridazine Carboxylic Acid, A Protected Piperazic Acid," *Synth. Comm.*, 18(18):2225–2231 (1988).

Schmidt, U., et al., "Enantioselective Syntheses of (R)– and (S)–Hexahydropyridazine–3–carboxylic Acid Derivatives," *Synthesis*, 223–229 (1996).

*Primary Examiner*—Bruck Kifle
(74) *Attorney, Agent, or Firm*—Andrea L.C. Robidoux; Vertex Pharmaceuticals Incorporated

(57) ABSTRACT

This invention provides a concise, asymmetric synthesis of piperazic acid and derivatives thereof, whereby either the (3S)- or (3R)-enantiomeric form may be obtained with high optical purity. (3S)-piperazic acid is derived from D-glutamic acid through an (R)-2,5-dihydroxyvalerate ester intermediate. After the hydroxy groups are converted to suitable leaving groups, such as mesylates, the ester is treated with a bis-protected hydrazine to provide the desired (3S)-piperazic acid derivative. The (3R) enantiomer of piperazic acid may be similarly obtained starting with L-glutamic acid. The method may also be used to obtain piperazic acid derivatives that have moderate optical purity or are racemic. By this method, piperazic acid derivatives may be obtained that are useful as intermediates for pharmacologically active compounds. For example, certain intermediates of this invention are useful for preparing caspase inhibitors, particularly inhibitors of ICE, through additional steps known in the art.

46 Claims, No Drawings

ASYMMETRIC SYNTHESIS OF PIPERAZIC ACID AND DERIVATIVES THEREOF

This application is a Continuation Application, under 37 C.F.R. §1.53(b), of International PCT application number PCT/US 01/13330 filed Apr. 25, 2001 which claims the benefit of U.S. Provisional Application Ser. No. 60/202,104 filed May 4, 2000 the contents of which are hereby incorporated by reference.

TECHNICAL FIELD OF THE INVENTION

This invention relates to a method for the asymmetric synthesis of piperazic acid and derivatives thereof. The method is useful for preparing compounds, especially biologically active compounds, that contain predominantly either a (3R)- or (3S)-piperazic acid moiety. Most particularly, the method may be used to prepare certain caspase inhibitors, such as inhibitors of interleukin-1β converting enzyme ("ICE").

BACKGROUND OF THE INVENTION

Piperazic acid is the common name for hexahydropyridazine-3-carboxylic acid. Since the 3-position bearing the carboxylic acid group is a chiral center, piperazic acid may exist in either the (3S) or (3R) enantiomeric form. The enantiopurity or optical purity of piperazic acid may be conventionally defined in terms of percent enantiomeric excess (%ee) which is the percent of the major enantiomer minus the percent of the minor enantiomer. A racemic mixture has an enantiomeric excess of zero.

The enantiomeric forms of piperazic acid derivatives are important intermediates in natural product synthesis and in the synthesis of biologically useful compounds having non-natural amino acids or peptidomimetic moieties. The angiotensin converting enzyme ("ACE")inhibitor, Cilazapril®, contains the S-isomer of piperazic acid (Adams et al., Synthetic Comm, 1988, 18, 2225). Recently a class of caspase inhibitors, particularly interleukin-1β converting enzyme ("ICE") inhibitors, have been described that also contain piperazic acid, preferably the S-enantiomer (U.S. Pat. Nos. 5,874,424; 5,756,466; 5,716,929; 5,656,627; and 6,204,261). Examples of other pharmacologically active molecules having a piperazic acid moiety include the monamycin family of antibiotics (Bevan et al., J. Chem. Soc. (C), 1971, 522), the azinothricin antitumor antibiotics (see Hale et al., Tetrahedron, 1996, 52, 1047 and references cited therein), verucopeptin (Suguwara et al., J. Antibiotics, 1993, 46, 928), the aurantimycins (Grafe et al., J. Antibiotics, 1995, 48, 119), the C5a antagonist L-156,602 (Hensens et al., J. Antibiotics, 1991, 44, 249), the immunosuppressant IC101 (Ueno et al., J. Antibiotics, 1993, 46, 1658), the oxytocin antagonist L-156,373 (Pettibone et al., Endocrinology, 1989, 125, 217), and the matylastin type-IV collagenase inhibitors (Ogita et al., J. Antibiotics, 1992, 45, 1723; Tamaki et al., Tetrahedron Lett., 1993, 34, 683; Tamaki et al., Tetrahedron Lett., 1993, 34, 8477). Several asymmetric syntheses of piperazic acid and derivatives thereof have been described [Aspinall et al., J. Chem. Soc. Chem. Commun., 1993, 1179; Decicco et al., Syn. Lett., p. 615 (1995); Schmidt et al., Synthesis, p. 223 (1996); Hale et al., Tetrahedron, 1996, 52, 1047; U.S. Pat. No. 5,716,929; and Attwood et al., J. Chem. Soc. Perkin 1, 1986, 1011).

Resolution of enantiomers of piperazic acid from a racemic mixture has been described by Hassell et al., J. Chem. Soc. Perk. Trans. I, pp. 1451 (1979). That method involves using a chiral amine to form a crystalline salt with piperazic acid that has been amino protected. The resulting chiral salt, which is a mixture of diastereomers, is then crystallized from an appropriate solvent to separate the desired isomer from the mixture.

The resulting isomer of piperazic acid may then be esterified by known techniques. Unfortunately, if certain esters are desired, such as the commonly used t-butyl ester, the esterification reaction is slow, low-yielding and may require special laboratory equipment (Hassall et al., supra; PCT publications WO 97/22619 and WO 95/35308).

These syntheses are not desirable on a large scale for one or more of the following reasons: too many steps, less than desirable yields, inconveniently low temperatures, or expensive reagents.

Accordingly, it would be desirable to have an asymmetric synthesis of piperazic acid that is amenable to large-scale synthesis and overcomes the aforementioned shortcomings or otherwise improves upon the current methods. It would also be desirable to have a method of resolving a racemic or enantiomerically enriched piperazic ester in its deprotected form which is stable and may be easily utilized in further reactions.

SUMMARY OF THE INVENTION

This invention provides a short, asymmetric synthesis of piperazic acid and derivatives thereof, whereby either the (3S)- or (3R)-enantiomeric form may be obtained with high optical purity. dihydroxyvalerate ester. After the hydroxy groups are converted to suitable leaving groups, such as mesylates, the ester is treated with a bis-protected hydrazine to provide the desired (3S)-piperazic acid derivative. The general scheme is shown below.

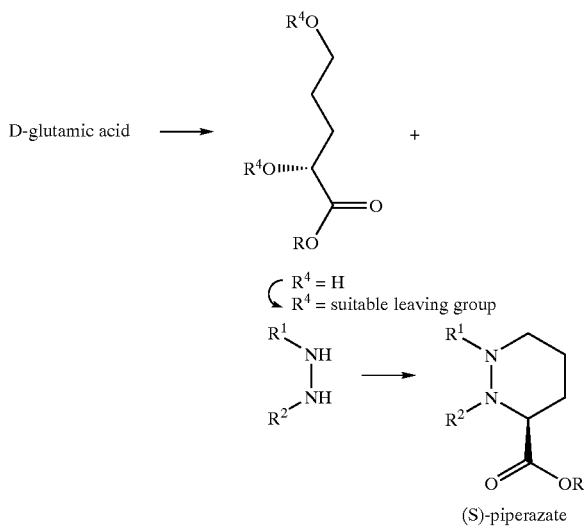

The (3R) enantiomer of piperazic acid may be similarly obtained starting with L-glutamic acid.

The invention also provides a novel method for preparing an enantiomerically enriched piperazic ester from racemic piperazic ester. The method involves the treatment of the piperazic ester with a commercially available enantiomerically enriched acid to produce a crystalline salt. This method is also useful for enhancing the %ee of a piperazic ester prepared by the synthesis of this invention or by other methods known in the art.

By this method, piperazic acid derivatives may be obtained that are useful as intermediates for pharmacologically active compounds. For example, certain intermediates of this invention are useful for preparing caspase inhibitors, particularly inhibitors of ICE, through additional steps known in the art.

DETAILED DESCRIPTION OF THE INVENTION

Some of the abbreviations used throughout the specifications (including in chemical formulae) are:

Bu=butyl
t-Bu=tert-butyl
Et=ethyl
Cbz=benzoyloxycarbonyl
BOC=tert-butyloxycarbonyl
Alloc=allyloxycarbonyl
Fmoc=fluorenylmethoxycarbonyl
DMF=N,N-dimethylformamide
THF=tetrahydrofuran
MTBE=methyl tert-butyl ether
DCM=dichloromethane
%ee=percent enantiomeric excess.

According to one embodiment, this invention provides a method for preparing a compound having the formula:

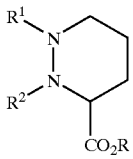

I wherein:
R is hydrogen or a carboxyl protecting group;
each $R^1$ and $R^2$ are independently selected from hydrogen or an amino protecting group, wherein $R^1$ and $R^2$ may be taken together to form a fused bicyclic or tricyclic amino protecting group; provided that $R^1$ and $R^2$ are not simultaneously hydrogen;
said process comprising the steps of:
(a) providing a compound of formula II:

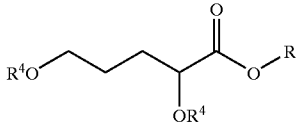

II wherein —$OR^4$ is a suitable leaving group, and
(b) treating II with a compound of formula III:

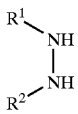

III in the presence of a suitable organic solvent, a suitable base, and optionally a water scavenger and/or a phase transfer catalyst, to produce I.

As used herein, the following definitions shall apply unless otherwise indicated. It is understood that combinations of substituents or variables are permissible only if such combinations result in stable compounds.

The term "stable compound", as used herein, refers to a compound sufficiently stable to allow manufacture and administration to a mammal by methods known in the art. Typically, such compounds are stable at a temperature of 40° C. or less, in the absence of moisture or other chemically reactive conditions, for at least a week.

Unless otherwise specified herein, a bond on a chiral carbon atom not depicted with stereochemistry as used herein means that the compound containing the chiral carbon atom may have a %ee between 0 to 100.

The term "carboxyl protecting group" refers to a moiety that prevents chemical reactions from occuring on the carboxyl group to which that protecting group is attached. A carboxyl protecting group must also be removable by a chemical reaction. Examples of carboxyl protecting groups include esters, such as methyl, ethyl, t-butyl, (un)substituted benzyl, and silyl esters, among others. Other carboxyl protecting groups are well known in the art and are described in detail in *Protecting Groups in Organic Synthesis*, Theodora W. Greene and Peter G. M. Wuts, 1991, published by John Wiley and Sons.

The term "amino protecting group" refers to a moiety that prevents chemical reactions from occuring on the nitrogen atom to which that protecting group is attached. An amino protecting group must also be removable by a chemical reaction. Examples of amino protecting groups include carbamates, such as BOC, Cbz, Fmoc, alloc, methyl and ethyl carbamates, among others; cyclic imide derivatives, such as phthalimide; amides, such as formyl, (un)substituted acetyl, and benzoyl; and trialkyl silyl groups, such as t-butyldimethylsilyl and triisopropylsilyl. Other amino protecting groups are well known in the art and are described in detail in *Protecting Groups in Organic Synthesis*, Theodora W. Greene and Peter G. M. Wuts, 1991, published by John Wiley and Sons.

When $R^1$ and $R^2$ taken together with their intervening atoms form a fused ring, a preferred fused ring is a phthalhydrazide.

The term "suitable organic solvent" refers to a solvent, or a mixture of two or more solvents, which induces conditions which are favorable for the reaction to proceed as intended. Suitable solvents for the alkylation reaction include, but are not limited to, polar, aprotic organic solvents such as DMF, DCM, THF, monoglyme, diglyme, and acetonitrile.

The term "suitable base" refers to a reagent, or a mixture of two or more reagents, which facilitates the displacement of a suitable leaving group by a nitrogen of hydrazine III in the alkylation reaction. Suitable bases for the alkylation reaction include, but are not limited to, hydroxides such as sodium hydroxide and lithium hydroxide, alkoxides such as potassium t-butoxide, carbonates of alkaline earth metals such as potassium and sodium carbonate, metal hydrides such as sodium hydride, fluorides such as tetraalkylammonium fluorides (e.g., tetrabutylammonium fluoride (TBAF)), potassium fluoride, cesium fluoride, tertiary organic amines such as 1,8-diazabicyclo[5.4.0]undecene-7 (DBU), and alkyl metals exemplified by the alkyl lithiums, such as the butyllithiums.

The present invention is particularly useful in an asymmetric synthesis for making non-racemic (3S)- or (3R)-piperazic acid derivatives. For the asymmetric route, an optically active or non-racemic valerate ester 3 is produced in step (a) from an optically active or non-racemic glutamic acid, as described below. Using this process, piperazic acid derivatives may be obtained having an enantiomeric excess greater than about 90%.

Scheme I

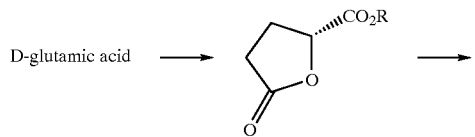

D-glutamic acid →

1, R = H
2, R = a carboxyl protecting group

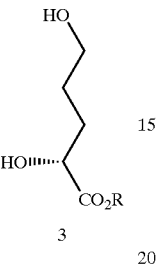

3

Non-racemic valerate esters of formula II may be obtained from D- or L-glutamic acid in a few steps following known chemistry. For example, as shown above in Scheme I, (R)-5-oxotetrahydrofuran-2-carboxylic acid (1) is accessible by treating D-glutamic acid with sodium nitrite in dilute sulfuric acid (Schmidt et al., 1996, *Synthesis*, 223; Qkabe et al., 1988, *J. Org. Chem.*, 53, 4780). Alternatively, the glutamic acid may be treated with potassium nitrite in dilute sulfuric acid or with nitric acid. The carboxylic acid 1 may be esterified by methods known in the art to provide the lactone ester 2, which in turn may be reduced with diisobutyl aluminum hydride (DIBAL) to give the (R)-2,5-dihydroxypentanoate ester 3. By this route, the ester 3 may be obtained with an optical purity of greater than about 90% ee, usually greater than about 95% ee (Ulrich et al., 1996, *Synthesis*, 226). The R carboxyl protecting group may be an ester, and most preferably t-butyl ester.

Scheme II

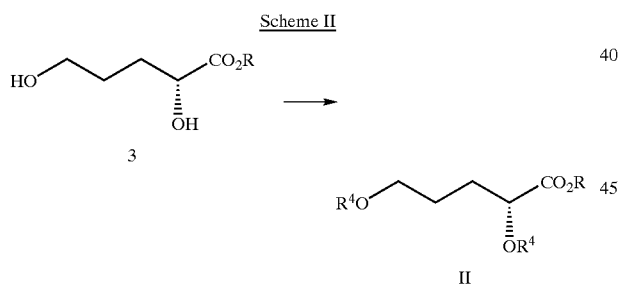

The valerate esters of formula II are obtained by converting the 2,5-dihydroxy groups of ester 3 to suitable leaving groups —$OR^4$, as shown in Scheme II above. A suitable leaving group is a group that will undergo displacement by a nitrogen of hydrazine III, especially in the presence of a base. Examples of suitable —$OR^4$ groups are known in the art (*Advanced Organic Chemistry*, Jerry March, Fourth Edition) and include alkyl- and arylsulfonates such as mesylate (—$OSO_2CH_3$), tosylate (—$OSO_2$-p-$C_6H_4$—$CH_3$), triflate (—$OSO_2CF_3$), nosylate (—$OSO_2$-p-$C_6H_4$—$NO_2$), brosylate (—$OSO_2$-p-$C_6H_4$—Br), and silyloxy groups such as t-butyldimethylsilyloxy (—$OSi(CH_3)_2C(CH_3)_3$). Methods for converting hydroxyl groups to such —$OR^4$ groups are well-known. For example, 2,5-dimesylvaleric ester may be obtained from the corresponding diol using methanesulfonyl chloride and triethylamine in dichloromethane according to standard methods (Qabar et al., 1996, *Tetrahedron Lett.* 37, 965).

Scheme III

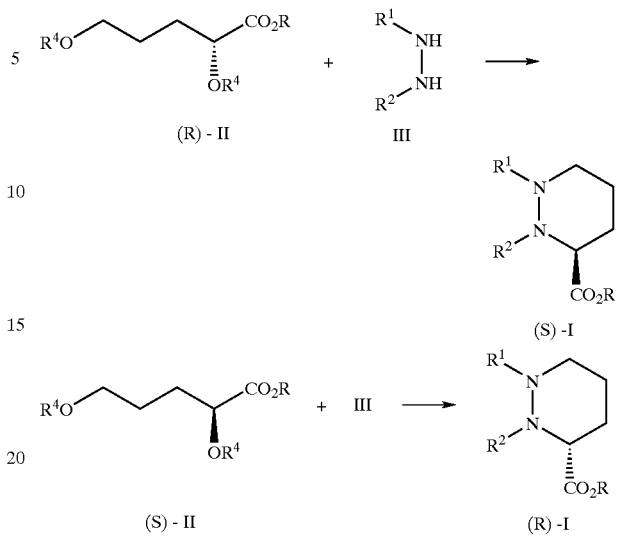

Scheme III above shows step (b) of the asymmetric process: the alkylation reaction of a compound of formula III with a non-racemic compound of formula II to provide the corresponding chiral piperazic acid of formula I. Valerate esters derived from either D- or L-glutamic acid as described above will typically have an enantiopurity of greater than 90% ee, preferably greater than 95% ee. Examples of preferred $R^1$ and $R^2$ groups include Cbz, BOC, alloc, Fmoc and other groups known in the art as amino protecting groups. $R_1$ and $R_2$ taken together may also be a phthalyl group such that hydrazine III is phthalhydrazide:

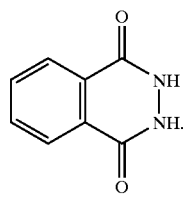

The N-alkylation reaction of hydrazine III shown in Scheme III is performed in a suitable organic solvent in the presence of a suitable base. DMF is a preferred solvent. The selection of the base will depend on the strength of the base, the choice of solvent, the temperature of the reaction, the optical purity that is desired and the nature of $R^1$, $R^2$, $R^4$ and R. Generally, the amount of base will be between about 2 to 5 mole equivalents based on the amount of bis-protected hydrazine to be alkylated. Preferred bases for obtaining chiral piperazates include the tetraalkylammonium fluorides such as TBAF.

The temperature at which the alkylation reaction is maintained will depend on the base and solvent, and may be in the range of −35° C. to 100° C., preferably in the range of about 20° C. to 80° C. The time of the reaction may vary from about 30 minutes to about 24 hours.

It is preferred that the alkylation reaction be performed under anhydrous or substantially anhydrous conditions. The best results are generally obtained using dry solvents and reagents. Therefore, a water scavenger may be optionally added to the reaction mixture. Any suitable water scavenger, such as sodium sulfate, may be used. The amount of water scavenger to be used will depend on the dryness of the starting solvents and reagents and their propensity to absorb moisture from the air under the reaction conditions and equipment set-up. Another optional reagent that may be added to the alkylation reaction is a phase transfer catalyst such as tetrabutylammonium iodide (TBAI) or tetrabutylammonium bromide (TBAB). When used, the amount of phase transfer catalyst will be in the range of about 0.01 to 1.0 mole equivalents based on the amount of hydrazine III to be alkylated. A preferred phase transfer catalyst is TBAI.

The optical purity of the chiral piperazate I obtained from the alkylation reaction will depend on the reaction conditions and the nature of the R, $R^1$, $R^2$, and $R^4$ groups. For example, when R is t-butyl, $R^1$ and $R^2$ are each Cbz and $R^4$ is mesyl, the use of TBAF in DMF at ambient temperature provides a piperazate I having an optical purity comparable to that of the starting valerate II. Under these conditions, either (R)- or (S)-I may be obtained having an optical purity that is about 90% ee or higher, preferably about 95% ee or higher. The use of potassium carbonate in DMF requires a temperature around 80° C. Under such conditions, alkylation of the hydrazine with a valerate ester that is 95% ee or higher will provide about a 70:30 mixture of enantiomers (40% ee). The use of sodium hydride in THF at ambient temperature provides only racemic piperazate. Choosing the necessary combination of base, solvent and temperature will be within the knowledge of one skilled in the art, by reference to the information described herein and the examples given below.

After the alkylation reaction is performed, the piperazic acid derivative I may optionally be separated from the reaction mixture by any standard means known in the art. The details of the conditions used for the methods described above are set forth in the Examples.

As described above, the optical purity of the piperazate I obtained by the synthetic method of this invention may vary according to the reaction conditions used. If desired, the resulting %ee may be further enhanced by a chiral resolution of a compound of formula IV

IV

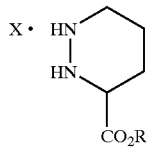

said method comprising the step of substantially separating the enantiomeric mixture using suitable physical means; wherein:

R is a carboxyl protecting group; and

X is a chiral agent.

The term "chiral agent" refers to an enantiomerically enriched group which may be ionically or covalently bonded to a nitrogen of a compound of formula IV. Chiral agents which are ionically bonded to said nitrogen include chiral acids. When the chiral agent is a chiral acid, the acid forms a diastereomeric salt with the piperazate nitrogen. The diastereomers are then separated by suitable physical means. Examples of chiral acids include, but are not limited to, tartaric acid, mandelic acid, malic acid, lo-camphorsulfonic acid, and Mosher's acid, among others. Chiral agents which may be covalently bonded to either of the piperazate nitrogens are known in the art.

The term "separated by suitable physical means" refers to methods of separating enantiomeric or diastereomeric mixtures. Such methods are well known in the art and include preferential crystallization, distillation, trituration, and crystallization, among others. Chiral agents and separation methods are described in detail in *Stereochemistry of Organic Compounds*, Eliel, E. L. and Wilen, S. H., 1994, published by John Wiley and Sons.

According to another embodiment, the present invention relates to compounds of formula IV:

IV

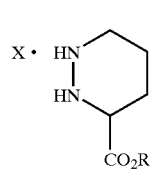

wherein:

R is a carboxyl protecting group; and

X is a chiral agent.

Compound IV may be prepared from I by removing the amino protecting groups $R^1$ and $R^2$. Methods for protecting group removal are well known in the art and described in *Protecting Groups in Organic Synthesis*, Theodora W. Greene and Peter G. M. Wuts, 1991. Compound IV is then formed by treating the resulting amino compound with a chiral agent, as shown in Scheme III below.

Scheme IV

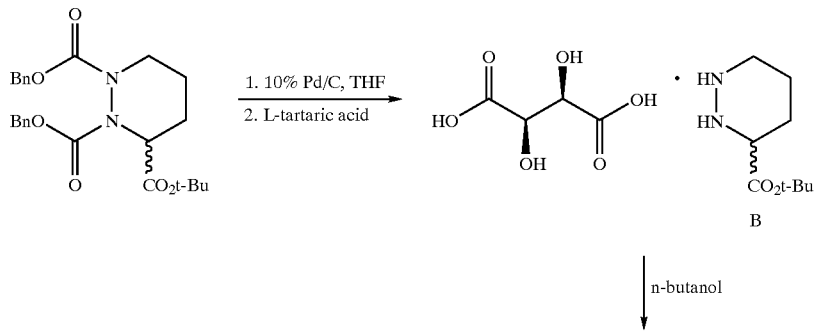

n-butanol

-continued

C

D

Using the resolution of racemic bis-Cbz, t-butyl piperazate as an example, Scheme IV above depicts the method of forming a compound of formula IV from a compound of formula I, where X is the chiral acid L-tartaric acid. The amino protecting groups were removed by hydrogenation and the resulting amino compound was treated with L-tartaric acid in n-butanol. Under these conditions, the (S)-t-butyl piperazate crystallized out of the solution and was readily isolated by filtration. Other chiral acids are well known to those skilled in the art. The details of the conditions used are set forth in the Examples hereinbelow.

Another embodiment of the present invention comprises the steps of deprotecting the compound of formula I and forming a diastereomeric mixture to provide a compound of formula IV:

IV wherein:
R is a carboxyl protecting group;
X is a chiral agent;
said process comprising the steps of:
(a) providing a compound of formula I;
(b) removing $R^1$ and $R^2$ to provide a compound of formula V; and

V (c) treating V with a chiral agent to form IV.

According to another preferred embodiment, the present invention relates to a method of enhancing the %ee of a racemic or enantiomerically enriched compound of formula IV

IV wherein:
R is a carboxyl protecting group; and
X is a chiral agent;
comprising the steps of:

(a) preparing a diastereomeric mixture of formula IV wherein:
R is a carboxyl protecting group; and
X is a chiral agent;
(b) combining IV with a solvent and heating to reflux to form a solution of IV;
(c) allowing said solution to cool to ambient temperature to cause precipitation of enantiomerically enriched IV; and
(d) filtering the suspension obtained at step (c) and collecting the precipitate, or filtering the suspension obtained at step (c) and collecting the filtrate.

The term "enantiomerically enriched", as used herein denotes that one enantiomer makes up at least 85% of the preparation. More preferably, the term denotes that at least 90% of the preparation is one of the enantiomers. Most preferably, the term denotes that at least 97.5% of the preparation is one of the enantiomers.

The term "enhancing the %ee" means that the method provides a piperazic acid derivative with a higher %ee than that of the piperazic acid derivative before using the method.

In a preferred embodiment, X is a chiral acid. In a most preferred embodiment, X is L-tartaric acid or D-tartaric acid. In this method, the use of L-tartaric acid causes precipitation of (S)-piperazic acid or an ester thereof. Conversely, the use of D-tartaric acid causes precipitation of (R)-piperazic acid or an ester thereof. It should be readily apparent to those skilled in the art that enantiomeric enrichment of one enantiomer in the precipitate causes an enantiomeric enrichment in the mother liquor of the other enantiomeric form. Therefore, according to another embodiment, the invention relates to a method of enhancing the %ee of a racemic or enantiomerically enriched compound of formula IV:

IV wherein:
R is a carboxyl protecting group; and
X is a chiral agent;
comprising the steps of:
(a) combining a compound of formula IV with a suitable solvent and heating to reflux to form a solution of IV;
(b) allowing said solution to cool to ambient temperature to cause precipitation of enantiomerically enriched IV; and (c) filtering the suspension obtained at step (b) and collecting the filtrate.

In either method it is preferred that the solvent is a $C_1$–$C_5$ straight or branched alkyl alcohol, most preferably n-butanol. A preferred chiral agent is tartaric acid and R is preferably t-butyl.

Compounds of formula IV where X is L- or D-tartaric acid are highly crystalline solids and readily allow for the separation of piperazate enantiomers. Accordingly, another embodiment relates to a compound of formula B, C, or D:

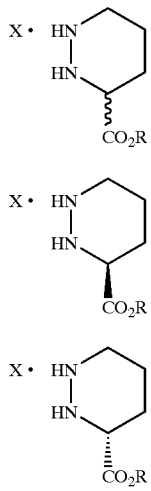

B

C

D wherein R is a carboxyl protecting group; and

X is a chiral agent, preferably L-tartaric acid or D-tartaric acid.

In another preferred embodiment, the precipitate is subjected to an additional crystallization step by adding more alcohol, heating to reflux and allowing the solution to cool to ambient temperature to cause precipitation and further enrichment of one enantiomer. This increases the relative amount of a single enantiomer in the preparation about 90% to greater than 97.5%.

According to another preferred embodiment, the invention relates to a method for preparing an enantiomerically enriched piperazic acid derivative, said method comprising the steps of:

(a) providing a compound of formula II:

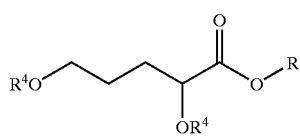

II wherein —$OR^4$ is a suitable leaving group;

(b) treating II with a compound of formula III:

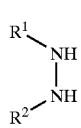

III in the presence of a suitable organic solvent and a suitable base to provide a compound of formula I;

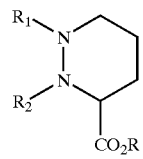

I (c) removing $R^1$ and $R^2$ to provide a compound of formula V;

V (d) treating V with a chiral agent to form a compound of formula IV; and

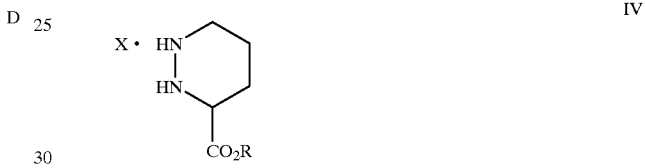

IV (e) substantially separating the enantiomeric mixture using suitable physical means to produce a compound of formula IV with an enhanced %ee;

wherein:
R is hydrogen or a carboxyl protecting group; and
each $R^1$ and $R^2$ are independently selected from hydrogen or an amino protecting group, wherein $R^1$ and $R^2$ may be taken together to form a fused bicyclic or tricyclic amino protecting group; provided that $R^1$ and $R^2$ are not simultaneously hydrogen; and
X is a chiral agent.

According to a preferred embodiment, the method of separating the enantiomeric mixture using suitable physical means comprises the steps:

(a) combining IV with solvent and heating to form a solution of IV;

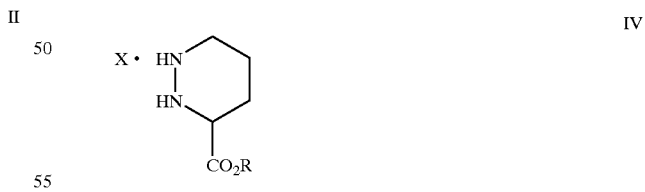

IV (b) allowing said solution to cool to cause precipitation of enantiomerically enriched IV; and (c) filtering the suspension obtained at step (b) and collecting the precipitate, or filtering the suspension obtained at step (b) and collecting the filtrate;

wherein:
R is hydrogen or a carboxyl protecting group; and
X is a chiral agent.

The compounds of formula IV or V may be converted in one step by known methods to a useful monoprotected piperazic ester VI.

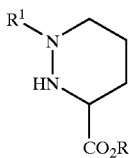

VI

A preferred compound of formula VI is the chiral compound of formula VI-a where R is t-butyl and R¹ is Cbz.

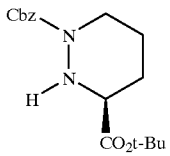

VI-a

The piperazic acid derivative VI may be obtained in chiral form as described above. Chiral VI, especially (S)-VI, is particularly useful as an intermediate for preparing certain pharmacologically active compounds, such as ICE inhibitors or prodrugs thereof exemplified by compound 4 shown below and described in U.S. Pat. Nos. 5,874,424; 5,756,466; 5,716,929; and 5,656,627 ("Vertex Patents") all of which are incorporated by reference. The conversion of piperazic ester VI, especially VI-a, to ICE inhibitors is known (Vertex Patents; Chen et al., 1999, Biorg. *Med. Chem. Lett.*, 9, 1587; Attwood et al., 1986, *J. Chem. Soc. Perkin Trans.* 1, 1011).

These ICE inhibitors have the general formula VII:

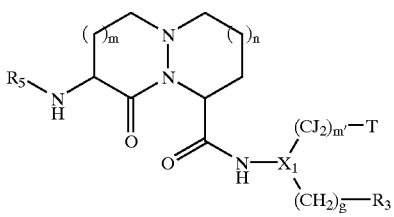

VII wherein:
any ring is optionally substituted at any substitutable carbon by $Q_1$, =O, —OH, —COOH, or halogen, and at any nitrogen by $R_5$;
$X_1$ is CH or N;
g is 0 or 1;
m and m' are independently 0, 1 or 2;
n is 0 or 1;
each J is independently selected from —H, —OH, or —F, provided that when a first and a second J are bound to a C, and said first J is —OH, then said second J is —H;
T is —$Ar_3$, —OH, —$CF_3$, —C(O) —C(O)—OH, —C(O)—OH or any biosteric replacement for —C(O)—OH;
$R_3$ is —CN, —CH=CH—$R_g$, CH=N—O—$R_g$, —(CH$_2$)$_{1-3}$—$T_1$—$R_9$, —CJ$_2$—$R_9$, —C(O)—$R_{13}$, or —C(O)—C(O) —N($R_5$)($R_{10}$);
$T_1$ is —CH=CH—, —O—, —S—, —SO—, —SO$_2$—, —NR$_{10}$—, —NR$_{10}$—C(O)—, —C(O)—, —O—C(O)—, —C(O) —O—, —C(O) —NR$_{10}$, O—C(O) —NR$_{10}$—, —NR$_{10}$—C(O)—O—, —NR$_{10}$—C(O)— NR$_{10}$—, —S(O)$_2$—NR$_{10}$—, —NR$_{10}$—S(O)$_2$—or —NR$_{10}$—S(O)$_2$—NR$_{10}$—;
each $R_5$ is independently selected from —H, —Ar$_1$, —C(O)—Ar$_1$, —S(O)$_2$—Ar$_1$, —R$_9$, —C(O)—NH$_2$, —S(O)$_2$—NH$_2$, —C(O)—R$_9$, —C(O) —O—R$_9$, —S(O)$_2$—R$_9$, —C(O) —N(R$_{10}$) (Ar$_1$), —S(O)$_2$—N (R$_{10}$) (Ar$_1$), —C(O)—N (R$_{10}$) (R$_9$), or —S(O)$_2$—N (R$_{10}$) (R$_9$);

each $R_9$ is a $C_{1-6}$ straight or branched alkyl group optionally singly or multiply substituted with —OH, —F, =O or Ar$_1$, wherein any $R_9$ may be substituted with a maximum of two Ar$_1$;

each $R_{10}$ is independently selected from —H or $C_{1-6}$ straight or branched alkyl;

$R_{13}$ is —H, —Ar$_1$, —R$_9$, —T$_1$—R$_9$ or —(CH$_2$)$_{1-3}$—T$_1$—R$_9$;

each Ar$_1$ is a cyclic group independently selected from a monocyclic, bicyclic or tricyclic aryl group containing 6, 10, 12 or 14 carbon atoms; a monocyclic, bicyclic or tricyclic cycloalkyl group containing between 3 and 15 carbon atoms, said cycloalkyl group being optionally benzofused; or a monocyclic, bicyclic or tricyclic heterocycle group containing between 5 and 15 ring atoms and at least one heteroatom group selected from —O—, —S—, —SO—, —SO$_2$—, =N—, or —NH—, wherein said heterocycle group optionally contains one or more double bonds and optionally comprises one or more aromatic rings;

Ar$_3$ is a cyclic group selected from phenyl, a 5-membered heteroaromatic ring or a 6-membered heteroaromatic ring, wherein said heteroaromatic rings comprise from 1–3 heteroatom groups selected from —O—, —S—, —SO—, —SO$_2$—, =N—, or —NH—;

wherein each Ar$_1$ or Ar$_3$ is optionally singly or multiply substituted at any ring atom by —NH$_2$, —C(O)—OH, —Cl, —F, —Br, —I, —NO$_2$, —CN, =O, —OH, -perfluoro $C_{1-3}$ alkyl,

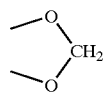

or —Q$_1$; and each $Q_1$ is independently selected from —Ar$_1$, —R$_9$, —T$_1$—R$_9$, or (CH$_2$)$_{1-3}$—T$_1$—R$_9$; provided that when —Ar$_1$ is substituted with a $Q_1$ which comprises one or more additional —Ar$_1$ groups, said additional —Ar$_1$ groups are not substituted with $Q_1$.

The method of this invention may be used in the synthesis of a compound of formula VII, wherein n is 1 and m is 2.

In another embodiment, the method of this invention may be used in the synthesis of a compound of formula VII, wherein $R_5$ is an acyl moiety selected from —C(O)—Ar$_1$, —C(O)—NH$_2$, —C(O)—R$_9$, —C(O)—O—R$_9$, —C(O)—N (R$_{10}$) (Ar$_1$), or —C(O)—N(R$_{10}$) (R$_9$).

In yet another embodiment, the method of this invention may be used in the synthesis of a compound of formula VII, wherein $X_1$ is CH; each J is H; m' is 1; T is —COOH or a biosteric replacement for —COOH; g is 0; and $R_3$ is —C(O)—R$_{13}$.

In a preferred embodiment, the method of this invention may be used in the synthesis of a compound of formula VII-a:

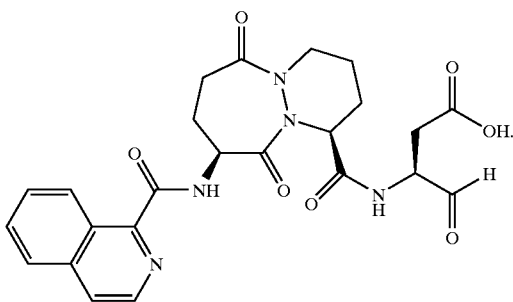

VII-a

Alternatively, the method of this invention may be used in the synthesis of a compound of the formula VIII:

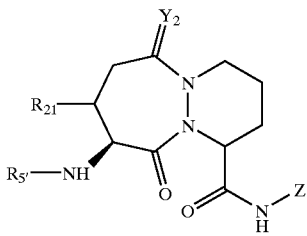

VIII wherein:

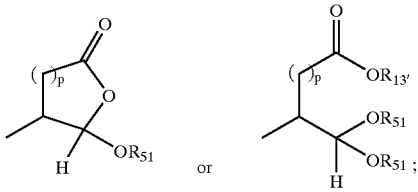

Z is selected from
p is 1 or 2;
each $R_5$, is independently selected from —C(O)—$R_{10'}$, —C(O)O—$R_9$, —C(O)—N ($R_{10'}$) ($R_{10'}$), —S(O)$_2$—$R_{9'}$, —S(O)$_2$—NH—$R_{10'}$, —C(O)—CH$_2$—O —$R_{9'}$, —C(O)C(O)—$R_{10'}$, —$R_{9'}$, —H, —C(O)C(O)—O$R_{10'}$, or —C(O)C(O)—N($R_{9'}$) ($R_{10'}$);
each $R_{9'}$ is independently selected from —Ar$_1$ or a —C$_{1-6}$ straight or branched alkyl group optionally substituted with Ar$_1$, wherein the —C$_{1-6}$ alkyl group is optionally unsaturated;
each $R_{10'}$ is independently selected from —H, —Ar$_1$, a —C$_{3-6}$ cycloalkyl group, or a —C$_{1-6}$ straight or branched alkyl group optionally substituted with Ar$_{3'}$, wherein the —C$_{1-6}$ alkyl group is optionally unsaturated;
$R_{13'}$ is selected from H, Ar$_1$, or a C$_{1-6}$ straight or branched alkyl group optionally substituted with Ar$_1$, —CONH$_2$, —OR$_{5'}$, —OH, —OR$_{9'}$, or —CO$_2$H;
each $R_{51}$ is independently selected from R$_{9'}$, —C(O)—R$_{9'}$, —C (O)—N(H)—R$_{9'}$, or two R$_{51}$ taken together form a saturated 4-8 member carbocyclic ring or heterocyclic ring containing —O—, —S—, or —NH—;
each $R_{21}$ is independently selected from —H or a —C$_{1-6}$ straight or branched alkyl group;
$Y_2$ is —H$_2$ or =O each Ar$_1$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, said heterocycle group optionally containing one or more double bonds, said heterocycle group optionally comprising one or more aromatic rings, and said cyclic group optionally being singly or multiply substituted by —Q$_1$;
each Q$_1$ is independently selected from the group consisting of —NH$_2$, —CO$_2$H, —Cl, —F, —Br, —I, —NO$_2$, —CN, =O, —OH, -perfluoro C$_{1-3}$ alkyl, R$_{5'}$, —OR$_{5'}$, —NHR$_{5'}$, OR$_{9'}$,

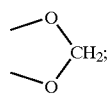

—N(R$_{9'}$)(R$_{10'}$), R$_{9'}$, —C(O)—R$_{10'}$, and
provided that when —Ar$_1$ is substituted with a Q$_1$ group which comprises one or more additional —Ar$_1$ groups, said additional —Ar$_1$ groups are not substituted with another —Ar$_1$.

Preferably, the method of this invention is used in the synthesis of a compound of formula VIII, wherein Y$_2$ is O and R$_{21}$ is H.

In another preferred embodiment, the method of this invention is used in the synthesis of a compound of formula VIII, wherein R$_{5'}$ is selected from —C(O)—R$_{10'}$, —C(O)O—R$_{9'}$, —C(O)—N(R$_{10'}$) (R$_{10'}$) —C(O)—CH$_2$—O —R$_{9'}$, —C(O)C(O)—R$_{10'}$, —C(O)C(O)—OR$_{10'}$, or —C(O)C(O)—N (R$_{9'}$) (R$_{10'}$).

In yet another preferred embodiment, the method of this invention is used in the synthesis of a compound of formula VIII, wherein Z is

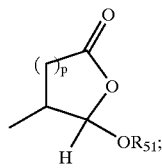

p is 1 and R$_{51}$ is selected from —Ar$_1$, —C$_{1-6}$ straight or branched alkyl or —C$_{1-6}$ straight or branched alkyl substituted with Ar$_1$.

A particularly preferred embodiment relates to using the method of this invention in the synthesis of ICE inhibitors 4 shown below.

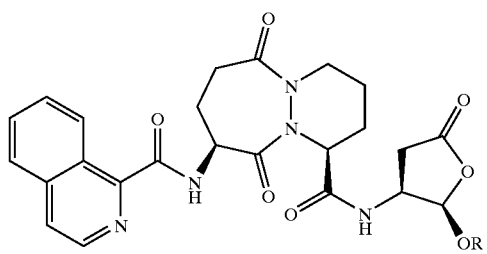

4-a, R=Et or 4-b, R=CH$_2$Ph

A key intermediate in the synthesis of the aforementioned ICE inhibitors is (1S, 9S)-9-amino-6,10-dioxo-1,2,3,4,7,8,9,10-octahydro-6H-pyridazino[1,2-a][1,2]diazepine-1-carboxylic acid (IX-a) having the "7,6" ring system. (S)-VI-a described above may be converted to IX-a and other useful intermediates having 7,6 ring system such as X and XI following known chemistry as shown in Scheme V.

8. Cyclization of 8 to form the 7,6 compound X was achieved by treating 8 with thionyl chloride and N-methylmorpholine in THF.

Compound X may be transformed to other useful intermediates having the 7,6 ring system by deprotecting either one or both of the protecting groups. By removing the phthalimide protecting group, compounds of formula IX are

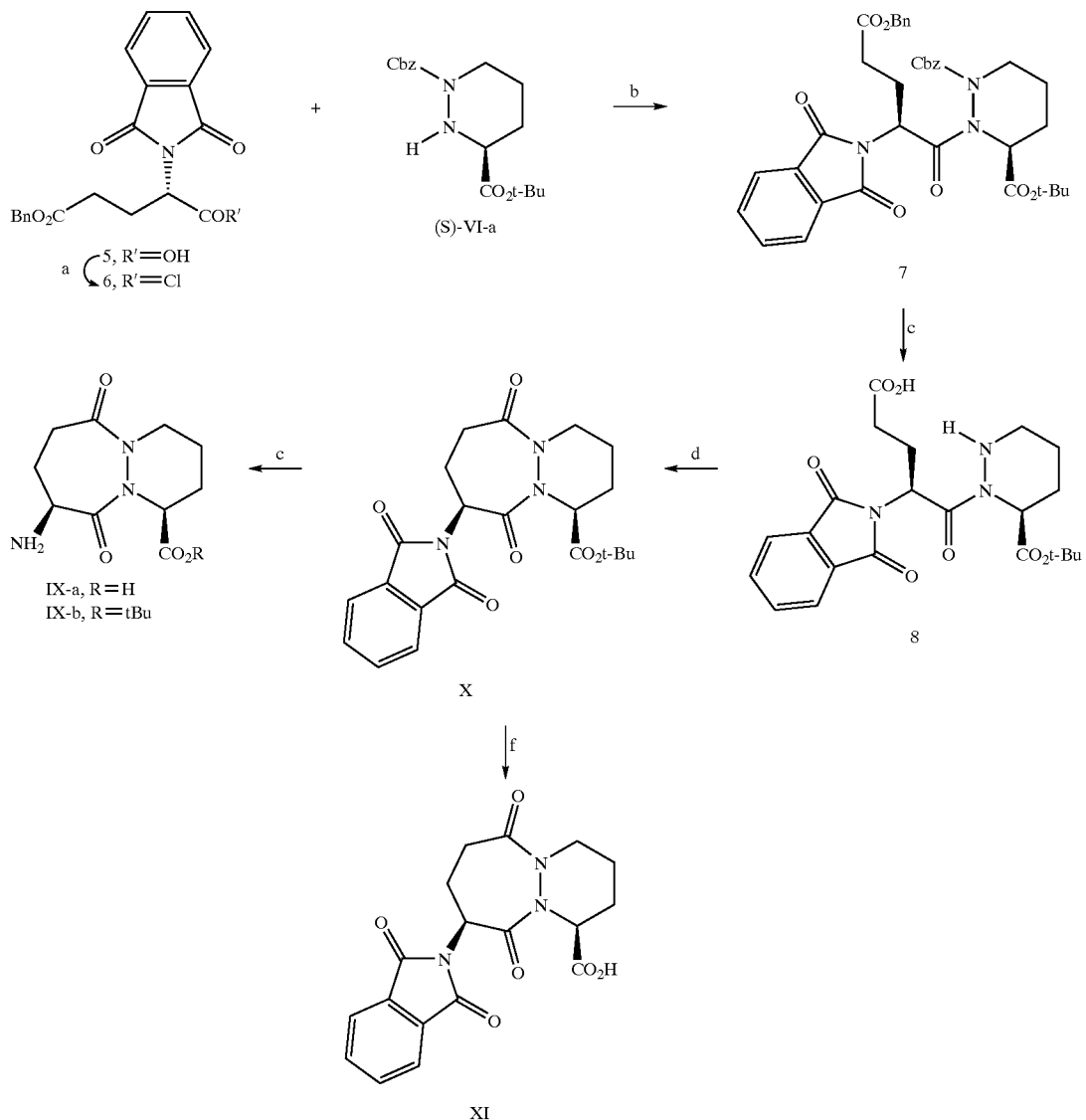

Scheme V

Reagents and conditions: (a) PCl$_5$, CH$_2$Cl$_2$; (b) NaHCO$_3$ (aq); (c) H$_2$, Pd/c, MeOH; (d) SOCl$_2$, N-methylmorpholine, THF; (e) hydrazine hydrate, EtOH; (f) 50% trifluoroacetic acid, CH$_2$Cl$_2$.

Scheme V above depicts the conversion of (S)-VI to compounds having the 7,6 ring system, specifically compounds IX, X, and XI. N-Phthaloylglutamic acid γ-benzyl ester (5) was converted to the acid chloride 6 with PCl$_5$ in CH$_2$Cl$_2$ under conditions well known in the art. Acid chloride 6 was coupled to (S)-VI-a in aqueous sodium bicarbonate to form the bis-Cbz intermediate 7. The two Cbz groups of compound 7 were simultaneously removed by hydrogenation in the presence of Pd/C in methanol to form obtained. By removing the ester, compounds of formula XI are obtained. The details of the conditions used for the above described synthetic steps are set forth in the Examples hereinbelow.

Using the preparation of compound 4 as an example, Scheme VI below depicts the synthesis of compounds of formula VIII from compound IX-b.

Scheme VI

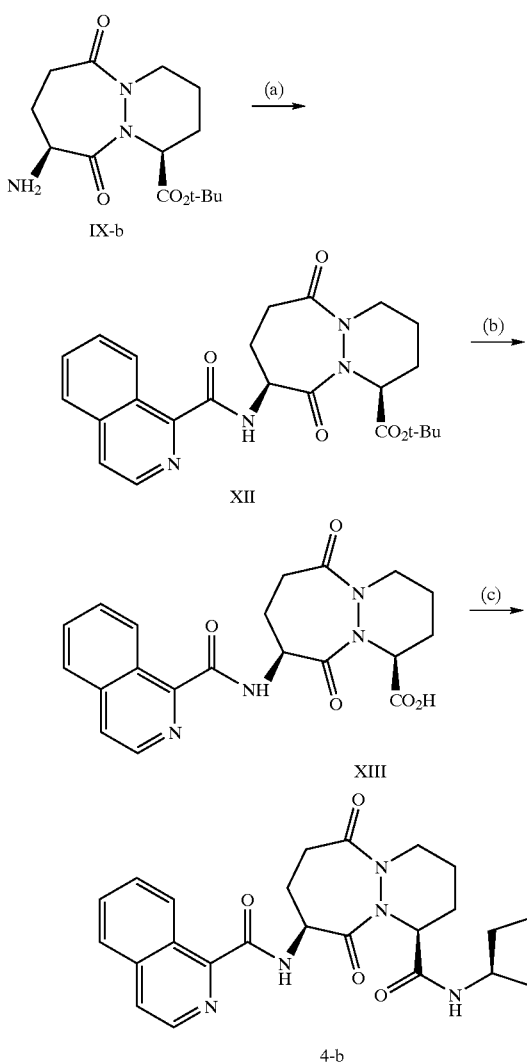

Compound 4-b may be prepared from IX-b by the methods described in U.S. Pat. No. 6,204,261, the disclosure of which is herein incorporated by reference.

In order that this invention be more fully understood, the following preparative examples are set forth. These examples are for the purpose of illustration only and are not to be construed as limiting the scope of the invention in any way.

EXAMPLE 1

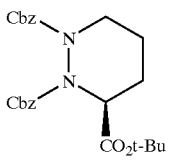

(S)-t-butyl- bis-(1,2-benzyloxycarbonyl)-hexahydropyridazine-3-carboxylate (>90% ee): To a solution of bis-Cbz hydrazine and (R)-t-butyl-2,5-dimesylvalerate (from the diol prepared by the method of Schmidt et al., *Synthesis*, p. 223 (1996)) in DMF was added $Na_2SO_4$ then TBAF (2.5 equivalents). The resulting reaction mixture was allowed to stir at room temperature for 24 hrs. The reaction was then diluted with ethyl acetate. The organic layer was washed sequentially with 10% citric acid and brine, dried over anhydrous $Na_2SO_4$ and concentrated in vacuo to afford the title compound. The optical purity of the title compound was greater than 90% ee as determined by HPLC using a ChiralPak® AD column and eluting with ethanol at 0.7 ml per minute.

EXAMPLE 2

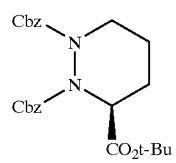

(S)-t-butyl-bis-(1,2-benzyloxycarbonyl)-hexahydropyridazine-3-carboxylate (40% ee): To a solution of bis-Cbz hydrazine and (R)-t-butyl-2,5-dimesylvalerate (96.5% ee) in DMF was added $Na_2SO_4$ then $K_2CO_3$ (5 equivalents) and TBAI (0.1 equivalents). The resulting reaction mixture was heated at 80° C. for 24 hrs. The reaction was allowed to cool and diluted with ethyl acetate. The organic layer was washed sequentially with 10% citric acid and brine, dried over anhydrous $Na_2SO_4$ and concentrated in vacuo to afford the title compound as a 70:30 mixture of the S:R enantiomers (40% ee, as determined by HPLC using a ChiralPak® AD column, eluting with ethanol at 0.7 ml/min).

EXAMPLE 3

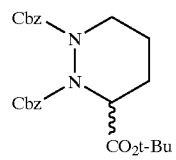

Racemic t-butyl-bis-(1,2-benzyloxycarbonyl)-hexahydropyridazine-3-carboxylate: To a solution of bis-Cbz hydrazine and (R)-t-butyl-2,5-dimesylvalerate (96.5% ee) in THF was added NaH (2 equivalents). The resulting reaction mixture was stirred at room temperature. The reaction was quenched then diluted with ethyl acetate. The organic layer was washed sequentially with 10% citric acid and brine, dried over anhydrous $Na_2SO_4$ and concentrated in vacuo to afford the title compound as a racemic mixture.

EXAMPLE 4

A. Deprotection and Salt Formation

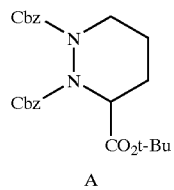

-continued

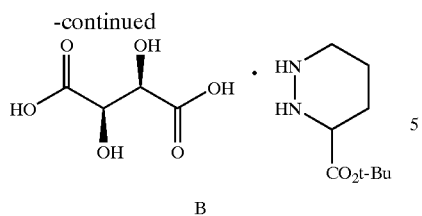

B

Hexahydro-pyridazine-3-carboxylic acid tert-butyl ester, L-tartaric acid salt (B): Compound A was combined with 10% Pd/C (10% w/w) in tetrahydrofuran. The resulting suspension was stirred at 60° C. under a hydrogen atmosphere until deprotection complete. The catalyst was removed via filtration, to the filtrate was added L-tartaric acid (1 equivalent) and the resulting solution concentrated in vacuo.

B. Enantiomeric Enrichment

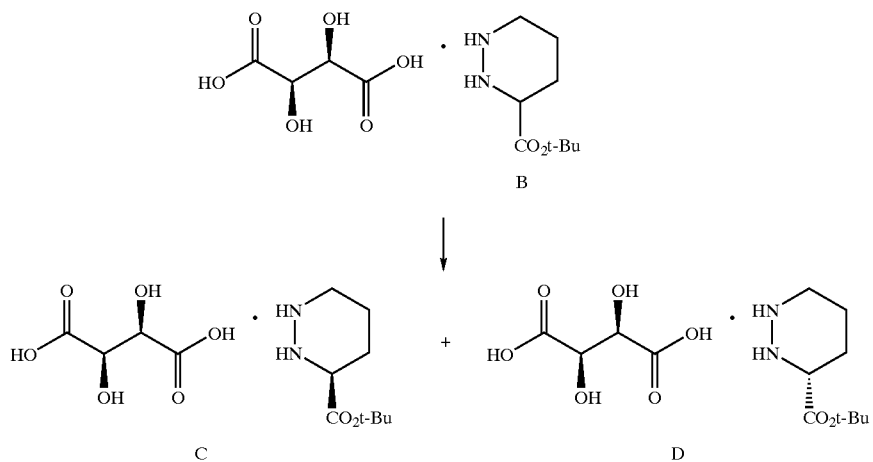

The concentrate (B) was taken up in n-butanol (10 volumes), heated to reflux, then allowed to slowly cool to ambient temperature while stirring. The resulting solids were collected via filtration to afford (S)-piperazic acid, t-butyl ester as the tartrate salt (C) in 33% yield.

C. Chiral Analysis

Compound (C) was suspended in water and DCM and cooled. We then added NaOH to basify the aqueous layer. The layers were then separated and to the organic layer we added two equivalents of benzyl chloroformate and NaOH. After stirring for 1 hour, the layers were again separated and the organic layer was washed with water. The organic layer was then dried over $MgSO_4$ and then concentrated in vacuo to produce the bis-Cbz piperazic acid, t-butyl ester for chiral HPLC analysis.

The bis-Cbz piperazic acid, t-butyl ester was applied to a Chiralpak AD HPLC column (Chiral Technologies, Exton, Pa.) and eluted with ethanol at 0.8 ml/minute. Fractions from the column were quantitate by absorption at 210 nm. The results demonstrated that (S)-piperazic acid, t-butyl ester accounted for 94.5% of the piperazic acid, t-butyl ester present in the preparation.

EXAMPLE 5

Conversion of Intermediate IV' to Intermediate VI-a

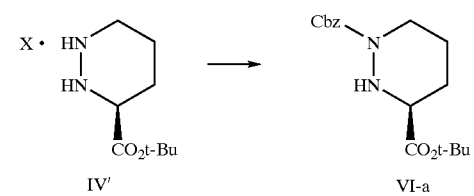

Tetrahydro-pyridazine-1,3-dicarboxylic acid 1-benzyl ester 3-tert-butyl ester (VI-a): Compound IV' (1 mmol) is combined with toluene and sodium hydroxide (aqueous, 2M, 3 equivalents) and the resulting mixture cooled to 1° C. A solution of benzylchloroformate (1.05 equivalents) in toluene is added while maintaining the reaction pH at 10 or higher by the addition of sodium hydroxide, as needed. After stirring an additional 1 hour, allow the mixture to warm to room temperature then extract with ethyl acetate. The organic layer is washed with brine, dried over sodium sulfate and concentrated to afford VI-a.

EXAMPLE 6

Conversion of Intermediate X to an Inhibitor of ICE

A. Phthalimide Removal to Form IX-b

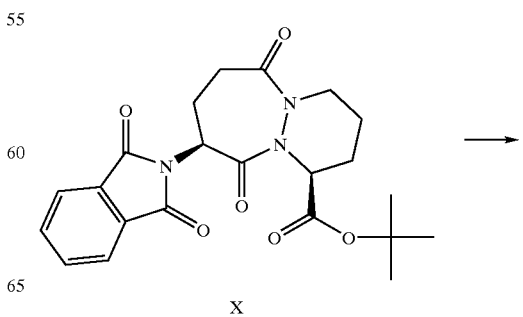

X

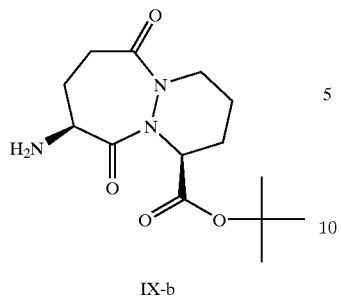

IX-b

C. t-Butyl Ester Hydrolysis to Form Compound XIII

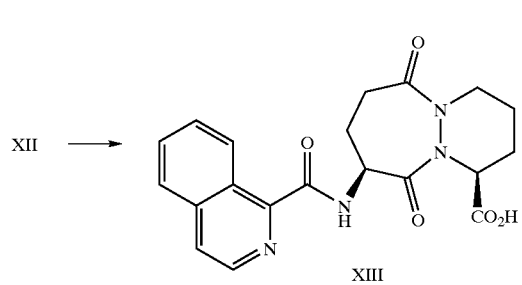

t-Butyl-9-amino-6,10-dioxo-1,2,3,4,7,8,9,10-octahydro-6-H-pyridazino[1,2-a][1,2]diazepine-1-carboxylate (GB 2,128,984): To a suspension of X (107 g, 0.25 mol) in ethanol (900 mL) was added hydrazine (27 mL, 0.55 mol) and the resulting mixture was allowed to stir at ambient temperature. After 4 hours, the reaction was concentrated in vacuo and the resulting white solid was suspended in acetic acid (1L of 2N) and allowed to stir at ambient temperature for 16 hours. The resulting white solid was filtered off and washed with water. The filtrate was made basic by the addition of solid sodium carbonate and the product extracted with dichloromethane. The organic layer was washed with brine, dried over magnesium sulfate and concentrated in vacuo to afford 79 g of compound IX-b as a yellow viscous oil.

B. Formation of Compound XII

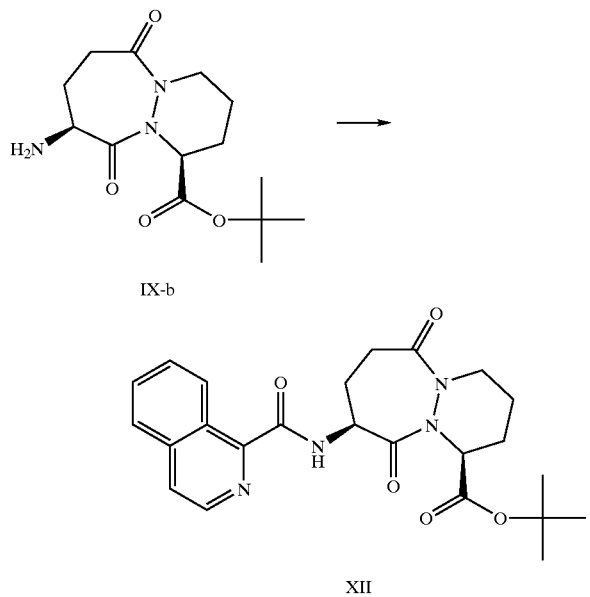

t-Butyl-9—(isoquinolin-1-oylamino)-6,10-dioxo-1,2,3,4,7,8,9,10-octahydro-6-H-pyridazino[1,2-a][1,2]diazepine-1-carboxylate (XII): To a solution of IX-b (79 g, 0.265 mol) and isoquinolin-1-carboxylic acid (56 g, 0.32 mol) in dichloromethane and DMF (400mL:400mL) was added hydroxybenzotriazole (54 g, 0.4 mol) and 1-(3-dimethylaminopropyl)-3-ethylcarbodiimide hydrochloride (74 g, 0.39 mol) and the resulting mixture was allowed to stir at ambient temperature for 16 hours. The reaction mixture was poured into water and extracted with ethyl acetate. The ethyl acetate layer was washed with 0.5N sodium bisulfate, water, sodium bicarbonate, brine, dried over sodium sulfate and concentrated in vacuo to afford 122 g of compound XII as an orange solid-foam.

9-(isoquinolin-1-oylamino)-6,10-dioxo-1,2,3,4,7,8,9,10-octahydro-6-H-pyridazino[1,2-a][1,2]diazepine-1-carboxylate (XIII): A solution of the ester XII (from step B) (122 g) in dichloromethane and trifluoroacetic acid (200 mL) was allowed to stir at ambient temperature for 16 hours. The reaction mixture was concentrated to a black oil which was then triturated with acetonitrile and ether to afford 98 g of compound XIII as a pale yellow solid.

D. Formation of Compound 4-b

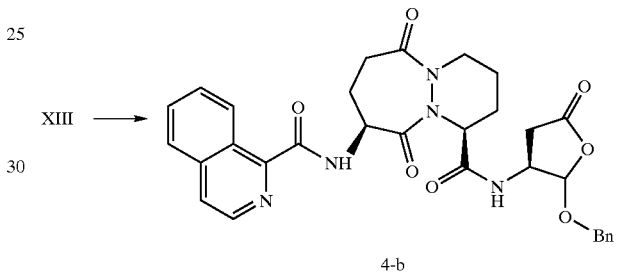

4-b

[1S, 9S (2RS, 3S)]N-(2-benzyloxy-5-oxotetrahydrofuran-3-yl)-6,10-dioxo-9-(isoquinolin-1-oylamino)-1,2,3,4,7,8,9,10-octahydro-6-H-pyridazino[1,2-a][1,2]diazepine-1-carboxamide (4-b): To a solution of (3S, 2RS) 3-allyloxycarbonylamino-2-benzyloxy-5-oxotetrahydrofuran [Bioorg. & Med. Chem. Lett., 2, pp. 615–618 (1992)] (4.4 g, 15.1 mmol) in dichloromethane was added N,N-dimethylbarbituric acid (5.9 g, 3.8 mmol) then tetrakispalladium(0) triphenyl phosphine (1.7 g, 1.5 mmol) and the resulting mixture was allowed to stir at ambient temperature for 15 minutes. To the resulting mixture was added the acid, compound XIII (from step C) (5.0 g, 12.6 mmol), hydroxybenzotriazole(2.0 g, 14.8 mmol), then 1-(3-dimethylaminopropyl)-3-ethylcarbodiimide hydrochloride (2.7 g, 14 mmol) and the reaction was allowed to stir for 3 hours at ambient temperature. The reaction mixture was then poured into water and extracted with ethyl acetate. The organics were washed with 0.5M sodium bisulfate, water, sodium bicarbonate, brine, dried over magnesium sulfate and concentrated in vacuo to afford 2.6 g of the crude product as a yellow foam. The crude material was purified by column chromatography ($SiO_2$, dichloromethane:acetone 9:1-3:1) to afford 1.2 g of the compound 4-b.

Compounds of formulae VII and VIII, and related compounds, that may be synthesized using the method of this invention as an intermediate step are described in WO 97/22619 and U.S. Pat. No. 6,204,261 the disclosure of which is herein incorporated by reference. Those related compounds may be synthesized from the product of the method of this invention, I, IV, or V, through modifications of the procedure set forth in Examples 4 through 6. Such modifications are well known in the art.

We claim:

1. A method for preparing a compound having the formula:

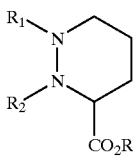

I wherein:
R is hydrogen or a carboxyl protecting group; and
each $R^1$ and $R^2$ are independently selected from hydrogen or an amino protecting group, wherein $R^1$ and $R^2$ may be taken together to form a fused bicyclic or tricyclic amino protecting group; provided that $R^1$ and $R^2$ are not simultaneously hydrogen;

said process comprising the steps of:
(a) providing a compound of formula II:

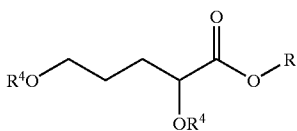

II wherein —$OR^4$ is a suitable leaving group; and
(b) treating II with a compound of formula III:

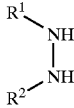

III in the presence of a suitable organic solvent and a suitable base to produce I.

2. The method according to claim 1, wherein said method further comprises the addition of a water scavenger in step (b).

3. The method according to either of claims 1 or 2, wherein said method further comprises the addition of a phase transfer catalyst in step (b).

4. The method according to claim 3, wherein said water scavenger is sodium sulfate and wherein said phase transfer catalyst is tetrabutylammonium iodide.

5. The method according to claim 1, wherein $R^1$ and $R^2$ are selected from benzyloxycarbonyl, t-butoxycarbonyl, or allyloxycarbonyl, or $R^1$ and $R^2$ taken together form a phthaloyl group.

6. The method according to claim 5, wherein $R^1$ and $R^2$ are both benzyloxycarbonyl.

7. The method according to claim 5, wherein $R^1$ and $R^2$ taken together form a phthaloyl group.

8. The method according to either of claims 1 or 6, wherein R is t-butyl.

9. The method according to claim 1, wherein said base is tetrabutylammonium fluoride, potassium carbonate, or sodium hydride.

10. The method according to claim 9, wherein said base is tetrabutylammonium fluoride.

11. The method according to claim 1, wherein said organic solvent is DMF, THF, or acetonitrile.

12. The method according to claim 11, wherein said solvent is DMF.

13. The method according to claim 1, wherein the compound of formula II and the compound of formula I are non-racemic.

14. The method according to claim 13, wherein the compound of formula II has an enantiomeric excess of at least about 90% of either the (R)-II enantiomer or the (S)-II enantiomer:

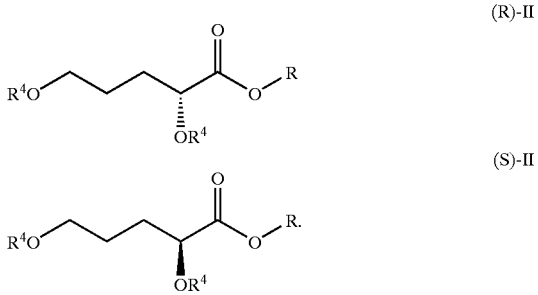

15. The method according to claim 14, wherein the compound of formula I is obtained having an enantiomeric excess of at least about 90%.

16. The method according to claim 14, wherein the compound of formula II has an enantiomeric excess of at least about 95% of either the (R)-II enantiomer or the (S)-II enantiomer.

17. The method according to claim 16, wherein the compound of formula I is obtained having an enantiomeric excess of at least about 95%.

18. The method according to claim 1, wherein said suitable leaving group is selected from a mesylate, tosylate, brosylate, nosylate, triflate, or t-butyl-dimethylsilyloxy group.

19. A method for preparing a compound of formula IV:

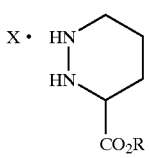

IV wherein:
R is a carboxyl protecting group; and
X is a chiral agent;
from a compound of formula I:

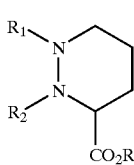

I wherein:
R is hydrogen or a carboxyl protecting group; and
each $R^1$ and $R^2$ are independently selected from hydrogen or an amino protecting group, wherein $R^1$ and $R^2$ may be taken together to form a fused bicyclic or tricyclic amino protecting group; provided that $R^1$ and $R^2$ are not simultaneously hydrogen;

said method comprising the step of treating a compound of formula V with the chiral agent to produce the compound of formula IV.

20. The method according to claim 19, wherein said compound of formula V is provided by:

(a) providing a compound of formula I; and (b) removing $R^1$ and $R^2$ to produce a compound of formula V

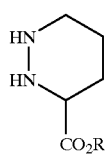

V

21. A method for enhancing the %ee of a first enantiomeric mixture of a compound of formula IV

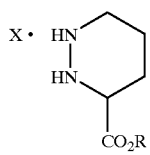

IV having a first %ee, said method comprising the step of substantially separating the enantiomeric mixture using suitable physical means to produce a second enantiomeric mixture of the compound of formula IV having a second %ee, wherein said second %ee is greater than said first %ee; wherein:

R is hydrogen or a carboxyl protecting group; and

X is a chiral agent.

22. The method according to claim 21 wherein said suitable physical means comprises the steps:

(a) combining IV with a solvent and heating to form a solution of IV;

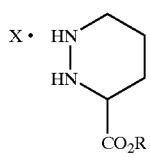

IV wherein:
R is hydrogen or a carboxyl protecting group; and
X is a chiral agent;

(b) allowing said solution to cool to cause precipitation of enantiomerically enriched IV; and (c) filtering the suspension obtained at step (b) and collecting the precipitate; or filtering the suspension obtained at step (b) and collecting the filtrate.

23. A method for preparing an enantiomerically enriched compound of formula IV, said method comprising the steps of:

(a) providing a compound of formula II:

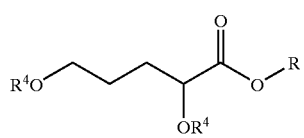

II wherein —$OR^4$ is a suitable leaving group;

(b) treating II with a compound of formula III:

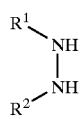

III in the presence of a suitable organic solvent and a suitable base to produce a compound of formula I;

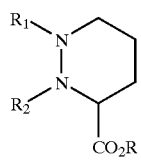

I (c) removing $R^1$ and $R^2$ to produce a compound of formula V;

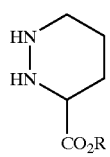

V (d) treating a compound of formula V with a chiral agent to form a compound of formula IV; and

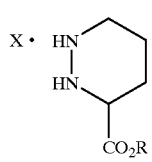

IV (e) substantially separating the enantiomeric mixture using suitable physical means to produce a compound of formula IV with an enhanced %ee;

wherein:
R is hydrogen or a carboxyl protecting group; and
each $R^1$ and $R^2$ are independently selected from hydrogen or an amino protecting group, wherein $R^1$ and $R^2$ may be taken together to form a fused bicyclic or tricyclic amino protecting group; provided that $R^1$ and $R^2$ are not simultaneously hydrogen; and
X is a chiral agent.

24. The method according to claim 23 wherein said suitable physical means comprises the steps:

(a) combining IV with an suitable solvent and heating to form a solution of IV;

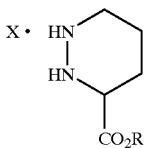

IV (b) allowing said solution to cool to cause precipitation of enantiomerically enriched compound of formula IV; and
(c) filtering the suspension obtained at step (b) and collecting the precipitate, or filtering the suspension obtained at step (b) and collecting the filtrate; wherein:
R is hydrogen or a carboxyl protecting group; and
X is a chiral agent.

25. The method according to claim 23, wherein R is t-butyl.

26. The method according to claim 23, wherein $R^1$ and $R^2$ are each independently selected from BOC, Cbz, or alloc.

27. The method according to claim 23, wherein $R^1$ and $R^2$ are taken together to form a phthalimide group.

28. The method according to claim 23, wherein X is L-tartaric acid or D-tartaric acid.

29. The method according to claim 24, wherein the solvent used in step (a) is n-butanol.

30. The method according to claim 23, wherein said base is TBAF.

31. The method according to any of claims 23–30, wherein said process further comprises the addition of a phase transfer catalyst at step (b).

32. The method according to claim 31, wherein said process further comprises the addition of a water scavenger at step (b).

33. The method according to claim 32, wherein said phase transfer catalyst is TBAI or TBAB.

34. The method according to either of claims 1 or 23, wherein the steps of said method are used in the synthesis of a compound of formula X:
wherein R is hydrogen or a carboxyl protecting group.

X

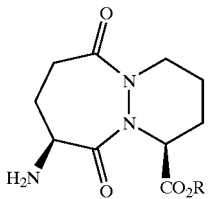

35. The method according to either or claims 1 or 23, wherein the steps of said method are used in the synthesis of a compound of formula VII:

VII

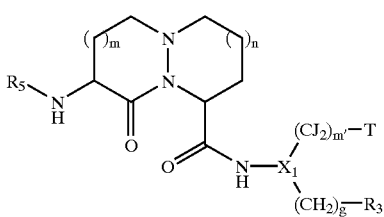

wherein:
any ring is optionally substituted at any substitutable carbon by $Q_1$, =O, —OH, —COOH, or halogen, and at any substitutable nitrogen by $R_5$;

$X_1$ is CH or N;
g is 0 or 1;
m and m' are independently 0, 1 or 2;
n is 0 or 1;
each J is independently selected from —H, —OH, or —F, provided that when a first and a second J are bound to a C, and said first J is —OH, then said second J is —H;
T is —$Ar_3$, —OH, —$CF_3$, —C(O)—C(O)—OH, —C(O)—OH or any biosteric replacement for —C(O)—OH;
$R_3$ is —CN, —CH=CH—$R_9$, CH=N—O—$R_9$, —$(CH_2)_{1-3}$—$T_1$—$R_9$, —$CJ_2$—$R_9$, —C(O)—$R_{13}$, or —C(O)—C(O)—N($R_5$)($R_{10}$);
$T_1$ is —CH=CH—, —O—, —S—, —SO—, —$SO_2$—, —$NR_{10}$—, —$NR_{10}$—C(O)—, —C(O)—, —O—C(O)—, —C(O)—O—, —C(O)—$NR_{10}$—, O, C(O)—$NR_{10}$—, —$NR_{10}$—C(O)—O—, —$NR_{10}$—C(O)—$NR_{10}$—, —S(O)$_2$—$NR_{10}$—, —$NR_{10}$—S(O)$_2$— or —$NR_{10}$—S(O)$_2$—$NR_{10}$—;
each $R_5$ is independently selected from —H, —$Ar_1$, —C(O)—$Ar_1$, —S(O)$_2$—$Ar_1$, —$R_9$, —C(O)—$NH_2$, —S(O)$_2$—$NH_2$, —C(O)—$R_9$, —C(O)—O—$R_9$, —S(O)$_2$—$R_9$, —C(O)—N($R_{10}$)($Ar_1$), —S(O)$_2$—N($R_{10}$)($Ar_1$), —C(O)—N($R_{10}$)($R_9$), or —S(O)$_2$—N($R_{10}$)($R_9$);
each $R_9$ is a $C_{1-6}$ straight or branched alkyl group optionally singly or multiply substituted with —OH, —F, =O or $Ar_1$, wherein any $R_9$ may be substituted with a maximum of two $Ar_1$;
each $R_{10}$ is independently selected from —H or $C_{1-6}$ straight or branched alkyl;
$R_{13}$ is —H, —$Ar_1$, —$R_9$, —$T_1$—$R_9$ or —$(CH_2)_{1-3}$—$T_1$—$R_9$;
each $Ar_1$ is a cyclic group independently selected from a monocyclic, bicyclic or tricyclic aryl group containing 6, 10, 12 or 14 carbon atoms; a monocyclic, bicyclic or tricyclic cycloalkyl group containing between 3 and 15 carbon atoms, said cycloalkyl group being optionally benzofused; or a monocyclic, bicyclic or tricyclic heterocycle group containing between 5 and 15 ring atoms and at least one heteroatom group selected from —O—, —S—, —SO—, —$SO_2$—, =N—, or —NH—, wherein said heterocycle group optionally contains one or more double bonds and optionally comprises one or more aromatic rings;
$Ar_3$ is a cyclic group selected from phenyl, a 5-membered heteroaromatic ring or a 6-membered heteroaromatic ring, wherein said heteroaromatic rings comprise from 1–3 heteroatom groups selected from —O—, —S—, —SO—, —$SO_2$—, =N—, or —NH—;
wherein each $Ar_1$ or $Ar_3$ is optionally singly or multiply substituted at any ring atom by —$NH_2$, —C(O)—OH, —Cl, —F, —Br, —I, —$NO_2$, —CN, =O, —OH, -perfluoro $C_{1-3}$ alkyl,

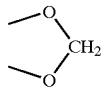

or —$Q_1$; and each $Q_1$ is independently selected from —$Ar_1$, —$R_9$, —$T_1$—$R_9$, or $(CH_2)_{1-3}$—$T_1$—$R_9$; provided that when —$Ar_1$ is substituted with a $Q_1$ which comprises one or more additional —$Ar_1$ groups, said additional —$Ar_1$ groups are not substituted with $Q_1$.

36. The method according to claim 35, wherein m is 2 and n is 1.

37. The method according to claim 36, wherein the terminal $R_5$ is selected from —C(O)—$Ar_1$, —C(O)—$NH_2$, —C(O)—R$_9$, —C(O)—O—R$_9$, —C(O)—N(R$_{10}$) (Ar$_1$), or —C(O)—N(R$_{10}$) (R$_9$).

38. The method according to claim 37, wherein: X$_1$ is CH; each J is H; m' is 1; T is —COOH or a biosteric replacement for —COOH; g is 0; and R$_3$ is —C(O)—R$_{13}$.

39. The method according to claim 38, wherein compound VII has the structure VII-a:

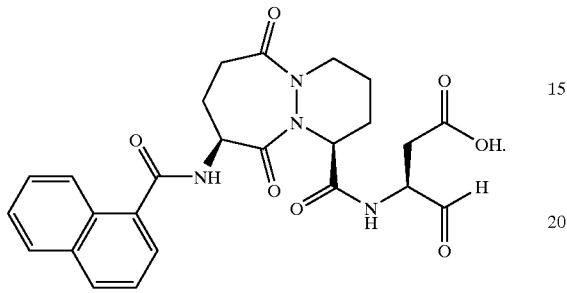

VII-a

40. The method according to either of claims 1 or 23, wherein said method is used as a step in the synthesis of a compound of the formula VIII:

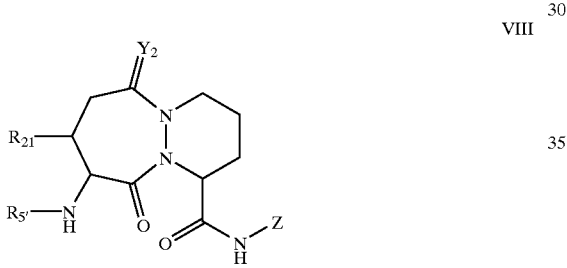

VIII wherein:

Z is selected from

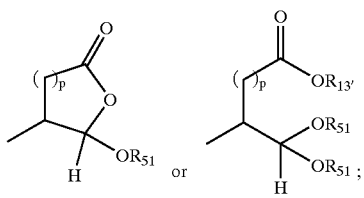

p is 1 or 2;

each R$_{5'}$ is independently selected from —C(O)—R$_{10'}$, —C(O)O—R$_9$, —C(O)—N(R$_{10'}$) (R$_{10'}$), —S(O)$_2$—R$_9$, —S(O)$_2$—NH—R$_{10'}$, —C(O)—CH$_2$—O—R$_9$, —C(O)C(O)—R$_{10'}$, —R$_9$, —H, —C(O)C(O)—OR$_{10'}$, or —C(O)C(O)—N(R$_9$) (R$_{10'}$); each R$_9$ is independently selected from —Ar$_1$ or a —C$_{1-6}$ straight or branched alkyl group optionally substituted with Ar$_1$, wherein the —C$_{1-6}$ alkyl group is optionally unsaturated;

each R$_{10'}$ is independently selected from —H, —Ar$_1$, a —C$_{3-6}$ cycloalkyl group, or a —C$_{1-6}$ straight or branched alkyl group optionally substituted with Ar$_3$, wherein the —C$_{1-6}$ alkyl group is optionally unsaturated;

R$_{13'}$ is selected from H, Ar$_1$, or a C$_{1-6}$ straight or branched alkyl group optionally substituted with Ar$_1$, —CONH$_2$, —OR$_{5'}$, —OH, —OR$_9$, or —CO$_2$H;

each R$_{51}$ is independently selected from R$_9$, —C(O)—R$_9$, —C(O)—N(H)—R$_9$, or two R$_{51}$ taken together form a saturated 4-8 member carbocyclic ring or heterocyclic ring containing —O—, —S—, or —NH—;

each R$_{21}$ is independently selected from —H or a —C$_{1-6}$ straight or branched alkyl group;

Y$_2$ is —H$_2$ or =O each Ar$_1$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, said heterocycle group optionally containing one or more double bonds, said heterocycle group optionally comprising one or more aromatic rings, and said cyclic group optionally being singly or multiply substituted by —Q$_1$; and each Q$_1$ is independently selected from the group consisting of —NH$_2$, —CO$_2$H, —Cl, —F, —Br, —I, —NO$_2$, —CN, =O, —OH, -perfluoro C$_{1-3}$ alkyl, R$_{5'}$, —OR$_{5'}$, —NHR$_{5'}$, OR$_9$,

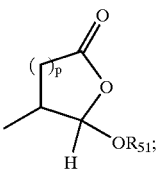

—N(R$_9$) (R$_{10'}$), R$_9$, —C(O)—R$_{10'}$, and provided that when —Ar$_1$ is substituted with a Q$_1$ group which comprises one or more additional —Ar$_1$ groups, said additional —Ar$_1$ groups are not substituted with another —Ar$_1$.

41. The method according to claim 40, wherein in compound VIII, Y$_2$ is O and R$_{21}$ is H.

42. The method according to claim 41, wherein in compound IX, R$_{5'}$ is selected from —C(O)—R$_{10'}$, —C(O)O—R$_9$, —C(O)—N(R$_{10'}$) (R$_{10'}$), —C(O)—CH$_2$—O—R$_9$, —C(O)C(O)—R$_{10'}$, —C(O)C(O)—OR$_{10'}$, or —C(O)C(O)—N(R$_9$) (R$_{10'}$).

43. The method according to claim 42, wherein in compound VIII,

Z is p is 1; and

R$^{51}$ is selected from —Ar$_1$, —C$_{1-6}$ straight or branched alkyl or —C$_{1-6}$ straight or branched alkyl substituted with Ar$_1$.

44. The method according to claim 43, wherein compound VIII has the structure 4:

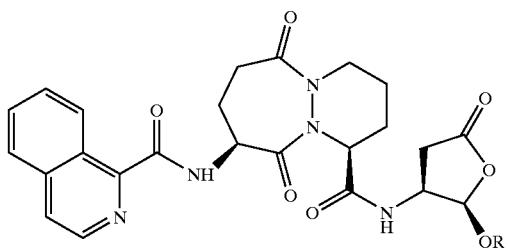
wherein R is ethyl or benzyl.
45. A compound of formula B, C, or D:
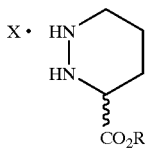
B
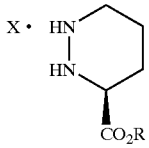
C
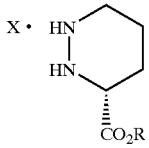
D
wherein R is a carboxyl protecting group; and
X is a chiral agent.
46. The compound according to claim 45 wherein X is L-tartaric acid or D-tartaric acid.
* * * * *